United States Patent [19]

Arika et al.

[11] Patent Number: 5,120,735
[45] Date of Patent: Jun. 9, 1992

[54] ANTIFUNGAL COMPOSITION

[75] Inventors: Tadashi Arika, Kasukabe; Mamoru Yokoo, Kawagoe; Kouji Amemiya, Kodaira; Tetsuya Maeda, Tokorozawa, all of Japan

[73] Assignee: Kaken Pharmaceutical Co., Ltd., Tokyo, Japan

[21] Appl. No.: 774,160

[22] Filed: Oct. 15, 1991

Related U.S. Application Data

[63] Continuation of Ser. No. 251,459, Sep. 30, 1988, abandoned.

[30] Foreign Application Priority Data

Oct. 2, 1987 [JP]  Japan ................... 62-249390

[51] Int. Cl.$^5$ ................ A61K 31/50; A61K 31/135; A61K 31/415; A61K 31/495
[52] U.S. Cl. ................... 514/252; 514/399; 514/646; 514/649
[58] Field of Search ................ 514/399, 646

[56] References Cited

FOREIGN PATENT DOCUMENTS 0164697 12/1985 European Pat. Off. .
0221781  5/1987 European Pat. Off. .
1579878 11/1980 United Kingdom .
2180239  3/1987 United Kingdom .
2185980  8/1987 United Kingdom .

OTHER PUBLICATIONS

Merck Index, 10 ed., (1983), pp. 762 and 885, 507, #3482.

Primary Examiner—Allen J. Robinson
Attorney, Agent, or Firm—Oblon, Spivak, McClelland, Maier & Neustadt

[57] ABSTRACT

A synergistically active antifungal composition comprising an azole compound and an arylmethylamine compound.

1 Claim, 2 Drawing Sheets

ANTIFUNGAL COMPOSITION

This application is a continuation of application Ser. No. 07/251,459, filed on Sept. 30, 1988, now abandoned.

The present invention relates to a synergistically active antifungal composition. More particularly, it relates to a synergistically active antifungal composition which exhibits excellent effects in the treatment of mycosis caused by microorganisms of e.g. Genus Candida, Genus Aspergillus or dermatophytes.

Bacterial infectious diseases have been almost completely under control by the development of excellent chemotherapeutic agents such as $\beta$-lactam antibiotics, aminoglucoside antibiotics, macrolide antibiotics and quinolonecarboxylic acid synthetic drugs. Whereas, fungal infectious diseases i.e. infectious deseases caused by Eumycetes such as fungi and yeast tend to increase year by year not only as superficial infection on the skin or in the vagina but also as systemic infection.

Particularly, in a case where the immunological competence has been lowered by extensive use of an antibacterial wide range antibiotic or a steroid hormone, or by use of an immunosuppressant or a carcinostatic substance, systemic infection such as deep-seated mycosis is frequented. However, the development of effective antifungal agents is far behind, since Eumycetes belong to eukaryotes like the higher animals as distinct from bacteria which are prokaryotes. It is thereby difficult to obtain a substance having a selective toxicity against Eumaycetes.

Antifungal agents presently available include polyene antibiotics such as amphotericin B and nystatin, azole antifungal agents such as clotrimazole, miconazole and ketoconazole and others such as griseofulvin and 5-fluorocytosine. However, they are inadequate in respect of the effectiveness or due to the toxicity.

For a patient having a lowered immunological competence, it is not sufficient that the drug has a fungistatic activity. Namely, the drug is required to have a fungicidal activity. However, the majority of presently available antifungal agents have poor fungicidal effects, whereby satisfactory effects can not be obtained. Azole antifungal agents such as clotrimazole and miconazole used to be employed for the local treatment as external application agents against tinea or Candidiasis. Recently, however, for example, miconazole (intravenous administration) or ketoconazole (oral administration) has been used against systemic infection such as Candidiasis, and successful results have been obtained. Active researches are being made in various countries of the world to develop azole antifungal agents. It is expected that azole drugs will be increasingly important as antifungal agents. However, the activities of the azole antifungal agents are fungistatic activities at a practically employed concentration. Therefore, satisfactory effects can not be obtained against infectious diseases where fungicidal effects are required, particularly when the immunological competence is lowered. On the other hand, in order to obtain the fungicidal effects, it will be required to administer a large amount of the drug whereby there will be problems of side effects or toxicity.

Accordingly, it is an object of the present invention to solve the above-mentioned drawbacks of the conventional antifungal agents, particularly the azole antifungal agents, and to provide a novel antifungal composition which exhibits excellent effects at a practical concentration.

To attain the above object, a study has been made on compositions prepared by combining various conventional antifungal agents. As a result, it has been found that a composition prepared by a combination of an azole antifungal agent and an arylmethylamine antifungal agent exhibits a remarkable synergistic effect, and it exhibits not only fungistatic activities but also fungicidal activities at a low dose.

The present invention provides a synergistically active antifungal composition comprising an azole compound and an arylmethylamine compound.

Now, the present invention will be described in detail with reference to the preferred embodiments.

Figure 1:
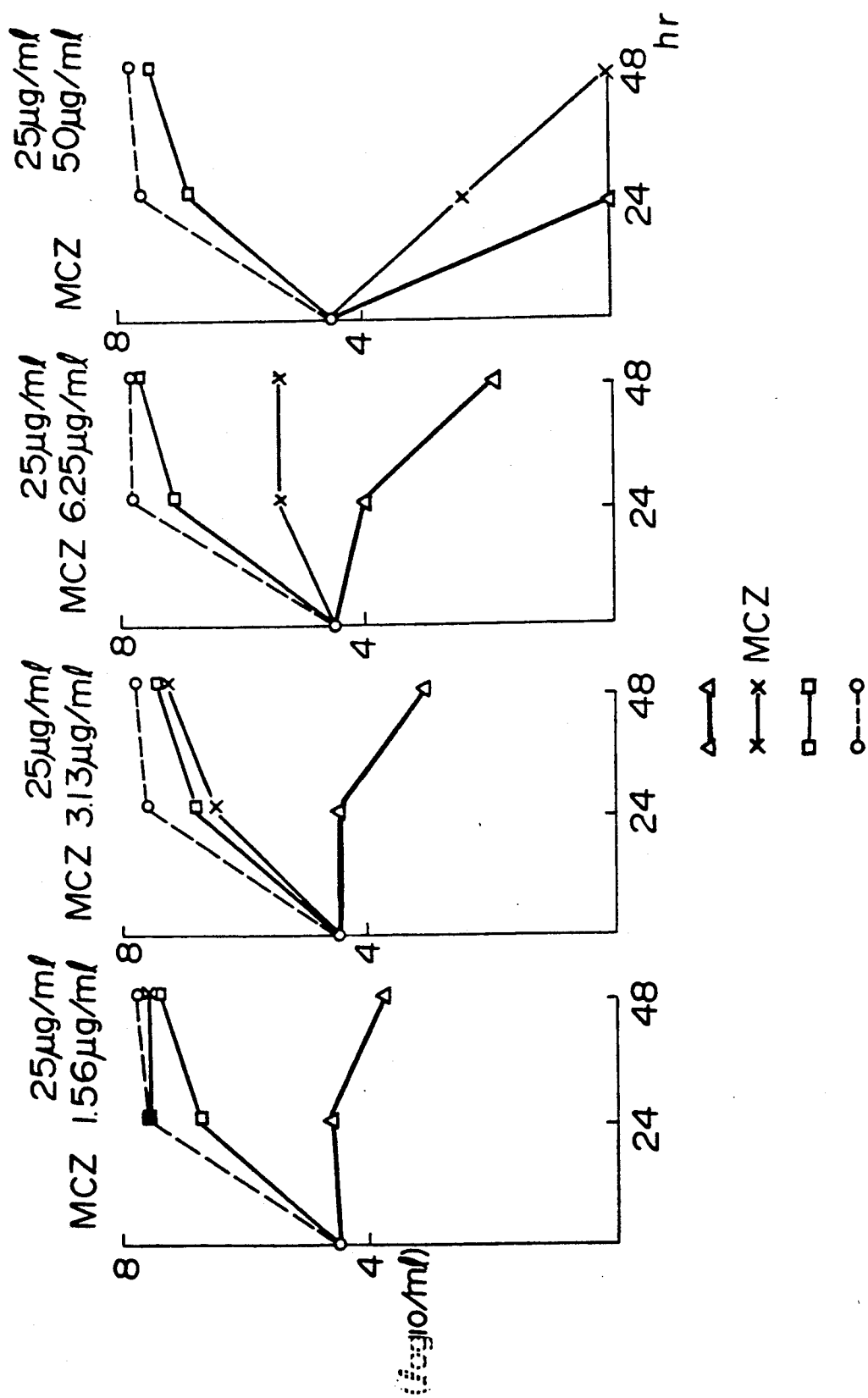
FIG. 1 shows graphs illustrating the influence of the combined use of Compound 1 as the arylmethylamine antifungal agent and miconazole as the imidazole antifungal agent over the growing curve of a fungus.

The azole antifungal agent to be used in the present invention is known. It includes imidazole antifungal agents and triazole antifungal agents.

Preferred imidazole antifungal agents include clotrimazole (Arzneim.-Forsh, Vol.22, p.1280 (1972)), miconazole (Arzneim.-Forsh., Vol.21, p.256 (1971)), econazole (Arzneim.-Forsh., Vol.25, p.224 (1975)), isoconazole (Arzneim.-Forsh., Vol.29, p.1344 (1979)), tioconazole (Antimicrobial Agents Chemotherapy, Vol.15, p.597-602 (1979)), sulconazole ("Eumycetes and mycosis", Vol.23, p.314-317 (1982)), oxiconazole (Arzneim.-Forsh., Vol.32, p.17-24 (1982)), cloconazole (J. Med. Chem., Vol.26, p.768-770 (1983)), bifonazole (Arzneim.-Forsh., Vol.33, p.517-524 (1983)), butoconazole (J. Med. Chem., Vol.21, p.840 (1978)), fenticonazole (Arzneim.-Forsh., Vol.31, p.2127 (1981)), zinoconazole (J. Med. Chem., Vol.26, p.442-445 (1983)) and ketoconazole (J. Med. Chem., Vol.22, p.1003-1005 (1979)).

Preferred triazole antifungal agents include terconazole (J. Med. Chem., Vol.26, p.611-613 (1983)), itraconazole (Antimicrobial Agents and Chemotherapy, Vol.26, p.5-9 (1984)), vibunazole Antimicrobial Agents and Chemotherapy, Vol. 25, p. 339-341 (1983) and fluconazole (Antimicrobial Agents and Chemotherapy, Vol.28, p.815-818 (1985)).

The antifungal composition of the present invention is prepared by incorporating an arylmethylamine antifungal agent to the above-mentioned azole antifungal agent.

This arylmethylamine antifungal agent is also known as disclosed in e.g. Japanese Unexamined Patent Publications No. 45/1986, No. 282348/1986, No. 131564/1977, No. 41855/1979, No. 32440/1981, No. 70335/1987, No. 201849/1987 and No. 201850/1987. It includes compounds of the following formulas:

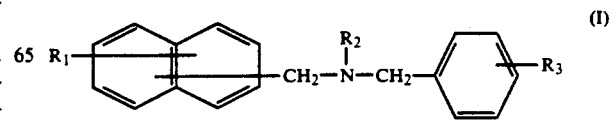

(I)

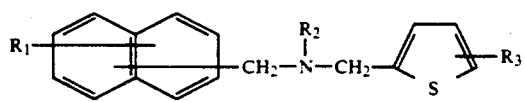

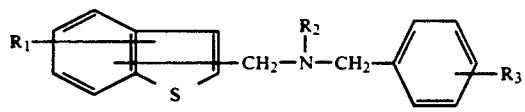

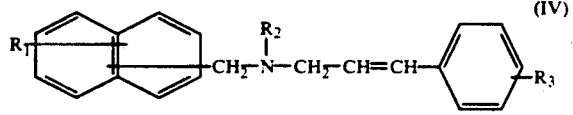

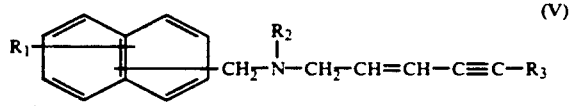

wherein $R_1$ is a member selected from group consisting of a hydrogen atom, a hydroxyl group, an alkoxy group, a nitro group, an alkyl group and a halogen atom, $R_2$ is a hydrogen atom or an alkyl group, and $R_3$ is a member selected from the group consisting of a hydrogen atom, an alkyl group, ja halogenated alkyl group, a nitro group and an aralkyl group.

Specific examples of the compounds of the formulas I to V are as follows:

Compounds of the Formula I (1) N-4-tert-butylbenzyl-N-methyl-1-naphthalenemethylamine (which corresponds to Compound 1 described hereinafter),
(2) N-4-tert-butylbenzyl-N-methyl-4-fluoro-1-naphthalenemethylamine. (which corresponds to Compound 3 described hereinafter),
(3) N-4-tert-butylbenzyl-N-ethyl-4-fluoro-1-naphthalenemethylamine,
(4) N-4-tert-butylbenzyl-N-methyl-4-chloro-1-naphthalenemethylamine,
(5) N-4-tert-butylbenzyl-N-methyl-4-bromo-1-naphthalenemethylamine,
(6) N-4-tert-butylbenzyl-N-methyl-4-iodo-1-naphthalenemethylamine,
(7) N-4-tert-butylbenzyl-N-methyl-2-methyl-1-naphthalenemethylamine,
(8) N-4-tert-butylbenzyl-N-methyl-4-methyl-1-naphthalenemethylamine,
(9) N-4-tert-butylbenzyl-N-methyl-2-hydroxy-1-naphthalenemethylamine,
(10) N-4-tert-butylbenzyl-N-methyl-2-methoxy-1-naphthalenemethylamine,
(11) N-4-tert-butylbenzyl-N-methyl-4-methoxy-1-naphthalenemethylamine,
(12) N-4-tert-butylbenzyl-N-methyl-5-nitro-1-naphthalenemethylamine,
(13) N-4-tert-butylbenzyl-1-naphthalenemethylamine,
(14) N-4-tert-butylbenzyl-N-ethyl-1-naphthalenemethylamine,
(15) N-methyl-N-4-tert-pentylbenzyl-1-naphthalenemethylamine (which corresponds to Compound 2 described hereinafter),
(16) N-ethyl-N-4-tert-pentylbenzyl-1-naphthalenemethylamine,
(17) N-4-tert-butylbenzyl-N-propyl-1-naphthalenemethylamine,
(18) N-butyl-N-4-tert-butylbenzyl-1-naphthalenemethylamine,
(19) N-methyl-N-2-methylbenzyl-1-naphthalenemethylamine,
(20) N-methyl-N-3-methylbenzyl-1-naphthalenemethylamine,
(21) N-methyl-N-3-trifluoromethylbenzyl-1-naphthalenemethylamine,
(22) N-methyl-N-4-methylbenzyl-1-naphthalenemethylamine,
(23) N-methyl-1-naphthalenemethylamine,
(24) N-methyl-N-4-propylbenzyl-1-naphthalenemethylamine,
(25) N-4-isopropyl-N-methyl-1-naphthalenemethylamine,
(26) N-4-butylbenzyl-N-methyl-1-naphthalenemethylamine,
(27) N-2-tert-butylbenzyl-N-methyl-1-naphthalenemethylamine,
(28) N-3-tert-butylbenzyl-N-methyl-1-naphthalenemethylamine,
(29) N-4-sec-butylbenzyl-N-methyl-1-naphthalenemethylamine,
(30) N-4-isobutylbenzyl-N-methyl-1-naphthalenemethylamine,
(31) N-methyl-4-pentylbenzyl-1-naphthalenemethylamine,
(32) N-methyl-N-4-tert-pentylbenzyl-1-naphthalenemethylamine,
(33) N-4-cyclohexylbenzyl-N-methyl-1-naphthalenemethylamine,
(34) N-4-fluorobenzyl-N-methyl-1-naphthalenemethylamine,
(35) N-4-bromobenzyl-N-methyl-1-naphthalenemethylamine,
(36) N-4-iodobenzyl-N-methyl-1-naphthalenemethylamine,
(37) N-methyl-N-4-nitrobenzyl-1-naphthalenemethylamine,
(38) N-4-(c,o-dimethylbenzyl)benzyl-N-methyl-1-naphthalenemethylamine.

Compound of the Formula II

(39) N-methyl-N-(1-naphthalenemethyl)-5-tert-butyl-2-thiophenemethylamine (which corresponds to Compound 5 described hereinafter).

Compound of the Formula III

(40) N-4-tert-butylbenzyl-N-methyl-3-benzo[b]thiophenemethylamine (which corresponds to Compound 4 described hereinafter),
(41) N-4-tert-butylbenzyl-N-ethyl-3-benzo[b]thiophenemethylamine,
(42) N-4-tert-butylbenzyl-N-methyl-7-methyl-3-benzo[b]-thiophenemethylamine, and
(43) N-4-tert-butylbenzyl-N-methyl-4-benzo[b]thiophenemethylamine.

Compound of the Formula IV

(44) (E)-N-cinnamyl-N-methyl-1-naphthalenemethylamine (which corresponds to Compound 6 described hereinafter).

Compound of the Formula V

(45) (E)-N-[6,6-dimethyl-2-hepten-4-ynyl]-N-methyl-1-naphthalenemethylamine (which corresponds to Compound 7 described hereinafter).

In the antifungal composition of the present invention, the weight ratio of the azole antifungal agent to the arylmethylamine antifungal agent may be varied within a wide range, but is preferably within a range of from 100:1 to 1:500, more preferably from 25:1 to 1:125. By mixing the azole antifungal agent and the arylmethylamine antifungal agent in the weight ratio within the above range, an excellent synergististic effect is obtainable in the treatment of mycosis.

In the composition of the present invention, it is particularly effective to reduce the proportion of the azole antifungal agent which has strong toxicity and unsuitable for administration in a large amount and to increase the proportion of the arylmethylamine antifungal agent having a low toxicity, whereby not only the above-mentioned synergistic effect but also the reduction of the toxicity of the drug can be attained.

The composition of the present invention is useful particularly for the treatment of superficial mycosis such as favus, tinea, eczema marginatum, oral thrush or cutaneous candidiasis, candidiasis of the vagina or urethra, or systemic candidiasis. It has particularly high activities against Candida albicans, whereby a high level of effectiveness is obtained against candidiasis.

The composition of the present invention can be adapted for local administration and can be incorporated in a usual pharmaceutical carrier in a wide range of concentrations (usually in an amount of from about 0.1 to about 10.0% by weight of the total composition) to prepare a formulation. The composition of the present invention may be formulated in the form of a cream drug or an ointment for external application, or in the form of a suppository or a liquid impregnated in a tampon for the use in the vagina.

Further, the composition of the present invention can be used for oral administration in the form of tablets, capsules or a liquid, and it may also be used for non-oral administration such as subcutaneous, intramuscular or intravenous injection.

Now, the present invention will be described in further detail with reference to Examples. However, it should be understood that the present invention is by no means restricted to such specific Examples.

EXAMPLE 1

Antifungal compositions were prepared by using various imidazole antifungal agents as the azole antifungal agent and a compound of the formula:

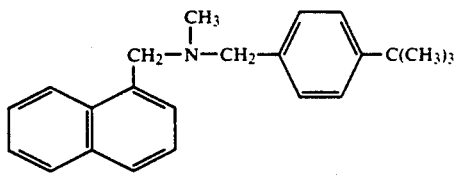

(hereinafter referred to simply as Compound 1) which is included in the above-formula I as the arylmethylamine antifungal agent, and they were subjected to the following tests (1), (2) and (3).

(1) The effects of the combined use of Compound 1 with various imidazole antifungal agents against Candida albicans MTU 12021 strain were examined as follows. Namely, drugs comprising Compound 1 and various imidazole antifungal agents were dissolved in dimethylsulfoxide (DMSO) to have a concentration of 10 mg/ml, and further diluted with DMSO to a level of one half of the concentration. Then, distilled water containing 0.1% by weight of Tween 80 was added thereto to obtain drug solutions having a concentration of from 1 to 1,000 μg/ml.

1 ml of each drug solution diluted twice was introduced into a sterilized Petri dish, and 8 ml of Sabouraud agar medium was added to prepare a agar plate. Thus, a series of agar plates for the combinations having various concentrations were prepared.

Candida albicans MTU 12021 strain cultured on a Sabouraud agar medium for 24 hours, was suspended in a saline, and a cells suspension having a concentration of $2 \times 10^6$ spores/ml was prepared by counting the number of spores by a hemacytometer. Then, 50 μl of the cells suspension was inoculated to the above agar plates by means of a microplanter (manufactured by Sakuma Seisakusho). The inoculated agar plates were cultured at 37° C. for 48 hours, whereupon the presence or absence of the growth of the strain was examined.

Table 1 shows the effects of the combined use of Compound 1 with various imidazole antifungal agents.

TABLE 1

| Aryl-methylamine antifungal agent | Minimum Inhibitory Concentration (MIC) μg/ml | | | | | |
|---|---|---|---|---|---|---|
| | Nil | Imidazole antifungal agent (μg/ml) | | | | |
| | | miconazole | econazole | isoconazole | oxiconazole | clotrimazole |
| Compound 1* | >100 | 1.56 | 1.56 | 1.56 | 6.25 | 3.13 |
| Nil | — | 25 | 25 | 25 | 100 | 12.5 |

Culture medium: Sabouraud agar medium
Culturing condition: 37° C. for 48 hours
Strain used: Candida albicans MTU 12021
*Concentration of Compound 1: 100 μg/ml As is evident from Table 1, remarkable synergistic effects are observed when Compound 1 is combined with an imidazole antifungal agent such as miconazole, econazole, isoconazole, oxiconazole or clotrimazole. The minimum inhibitory concentration can be reduced to a level of from ¼ to 1/16 as compared with the single use of the respective imidazole antifungal agents, and an increase in the antifungal activities is observed.

Further, the effect of the combined use of Compound 1 with miconazole and the effect of the combined use of Compound 1 with ketoconazole were examined by a checker board method, and the results are shown in Tables 2 and 3, respectively. Remarkable syntergistic effects are observed by the combined use of the Compound 1 with miconazole or ketoconazole.

TABLE 2

| | | Miconazole (μg/ml) | | | | | | | | | |
|---|---|---|---|---|---|---|---|---|---|---|---|
| | | 100 | 50 | 25 | 12.5 | 6.25 | 3.13 | 1.56 | 0.78 | 0.39 | 0 |
| Compound 1 (μg/ml) | 100 | − | − | − | − | − | − | − | + | + | + |
| | 50 | − | − | − | − | − | − | − | + | + | + |
| | 25 | − | − | − | − | − | − | + | + | + | + |
| | 12.5 | − | − | − | − | + | + | + | + | + | + |
| | 6.25 | − | − | + | + | + | + | + | + | + | + |
| | 3.13 | − | − | + | + | + | + | + | + | + | + |
| | 0 | − | − | + | + | + | + | + | + | + | + |

Culture medium: Sabouraud agar medium
Culturing condition: 37° C. for 48 hours
Strain used: *Candida albicans* MTU 12021
+: Growth observed
−: No growth observed

TABLE 3

| | | Ketoconazole (μg/ml) | | | | | | | | | | | |
|---|---|---|---|---|---|---|---|---|---|---|---|---|---|
| | | 100 | 50 | 25 | 12.5 | 6.25 | 3.13 | 1.56 | 0.78 | 0.39 | 0.2 | 0.1 | 0 |
| Compound 1 (μg/ml) | 100 | − | − | − | − | − | − | − | − | − | − | + | + |
| | 50 | − | − | − | − | − | − | − | − | − | − | + | + |
| | 25 | − | − | − | − | − | − | − | − | − | − | + | + |
| | 12.5 | − | − | − | − | − | − | − | − | − | − | + | + |
| | 6.25 | − | − | − | − | − | − | − | − | − | − | + | + |
| | 3.13 | − | − | − | − | − | − | − | − | − | − | + | + |
| | 1.56 | − | − | − | − | − | − | − | − | − | + | + | + |
| | 0.78 | − | − | − | − | + | − | + | + | + | + | + | + |
| | 0.39 | − | − | − | + | + | + | + | + | + | + | + | + |
| | 0 | − | − | − | + | + | + | + | + | + | + | + | + |

Culture medium: Sabouraud agar medium
Culturing condition: 37° C. for 48 hours
Strain used: *Candida albicans* MTU 12021
+: Growth observed
−: No growth observed For the purpose of comparison, similar tests were conducted by using Compound I and the following antifungal agents (non-azole antifungal agents) other than the azole antifungal agents.

Non-azole Antifungal Agents Combined with Compound 1

Siccanine

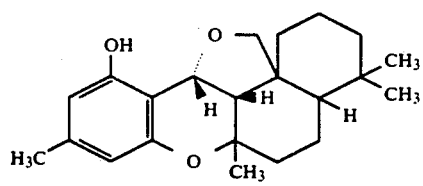

Haloprozin

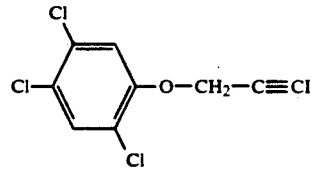

Pyrrolnitrin

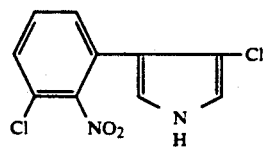

Amphotericin B

-continued

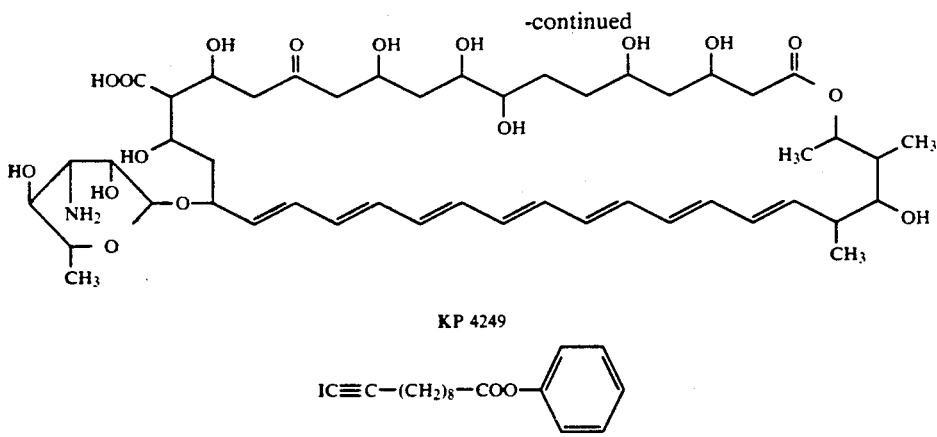

KP 4249

IC≡C—(CH₂)₈—COO—⟨phenyl⟩

The results are shown in Table 4. As is evident from Table 4, no synergistic effects were observed by the combined use of Compound 1 with the non-azole antifungal agents.

TABLE 4

| Aryl-methylamine antifungal agent | Minimum Inhibitory Concentration (MIC) μg/ml | | | | | |
|---|---|---|---|---|---|---|
| | Non-azole antifungal agents (μg/ml) | | | | | |
| | Nil | Sicca-nine | Halo-prozin | Pyrrol-nitrin | Amphote-ricin B | KP-4249 |
| Compound 1* | >100 | 25 | >100 | 50 | 3.13 | 100 |
| Nil | — | 25 | >100 | 50 | 3.13 | 100 |

Culture medium Sabouraud agar medium
Culturing condition 37° C. for 48 hours
Strain used Candida albicans MTU 12021
*Concentration of Compound 1: 100 μg/ml (2) The influence of the combined use of Compound 1 with miconazole as an imidazaole antifungal agent over the growth curve was examined.

Candida albicans MTU 12021 strain was inoculated to a Sabouraud liquid medium to have a concentration of about $2 \times 10^4$ spores/ml, and Compound 1 and miconazole were added separately or in combination, followed by shake culturing at 37° C. Upon expiration of 24 hours and 48 hours, 0.1 ml of the culture medium was sampled and spread on a Sabouraud agar plate containing 0.5% of yeast extract, followed by culturing at 37° C. for 48 hours. Then, the number of colonies were counted to determine the number of survived fungi.

The results are shown in FIG. 1. As shown in FIG. 1, it has been confirmed that the fungistatic or fungicidal effects were enhanced by Compound 1 by the combined use of Compound 1 with miconazole.

(3) The effects of the combined use of Compound 1 with miconazole or ketoconazole were examined by a disk method.

Candida albicans MTU 12021 stain was mixed with a Sabouraud agar medium to have a concentration of $5 \times 10^4$ spores/ml, and 10 ml thereof was poured into a sterilized Petri dish to obtain an inoculated agar plate.

50 mg of each of Compound 1, miconazole and ketoconazole was impregnated to a disk (Toyo Filter paper of 8 mm in diameter), and the disk was placed on the inoculated agar plate, followed by culturing at 37° C. for 96 hours, whereupon the synergistic effects were evaluated based on the growth inhibition ring thereby appeared.

Figure 2:
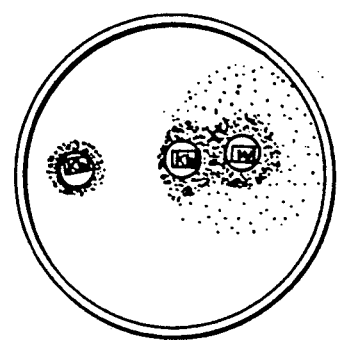
FIGS. 2 and 3 are views showing the results of the disk method tests to confirm the effects of the combined use of an arylmethylamine antifungal agent (Compound 1) and an azole antifungal agent (miconazole or ketoconazole).

FIG. 2 illustrates the effects of the combined use of Compound 1 with miconazole obtained by this disk method. In this Figure, the disks placed at the left and the center are disks of Compound 1, and the disk placed at the right is the disk of miconazole. Along the periphery of the miconazole disk at the right, a complete inhibitory ring with a small diameter and an incomplete inhibitory ring with a large diameter are observed, and by the Compound 1 disk at the center located substantially on the pheriphery of the incomplete inhibitory ring, a portion of the incomplete inhibitory ring is completely inhibited and connected to the above-mentioned complete inhibitory circle with a small diameter. This indicates distinct effects of the combined use of the Compound 1 with miconazole.

Figure 3:
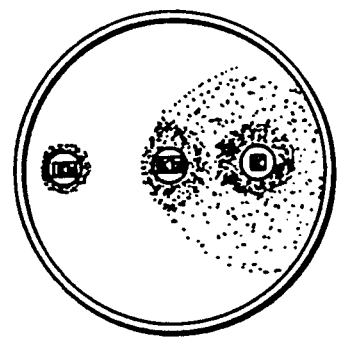

FIG. 3 is a view similar to FIG. 2 and illustrates the effects of the combined use of Compound 1 with ketoconazole according to the disk method. In this case, the combination of Compound 1 with ketoconazole exhibited remarkable effects of the combined use as in the case of the combination of Compound 1 with miconazole.

EXAMPLE 2

Various antifungal compositions were prepared by using the following Compounds 2 to 7 as the arylmethylamine antifungal agent and miconazole and ketoconazole as the imidazole antifungal agents, and they were subjected to the following tests (1) and (2).

Compound 2 (Which is Included in the Compounds of the Formula I)

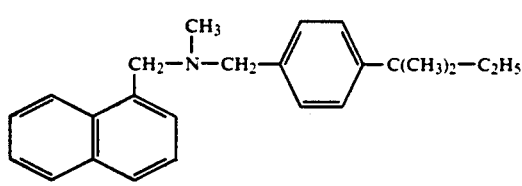

Compound 3 (Which is Included in the Compounds of the Formula I)

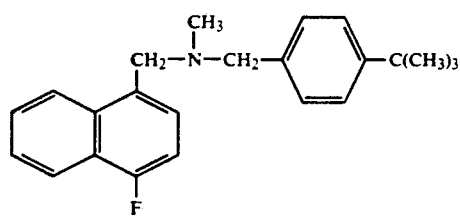

Compound 4 (Which is Included in the Compounds of the Formula III)

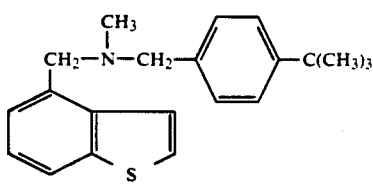

Compound 5 (Which is Included in the Compounds of the Formula II)

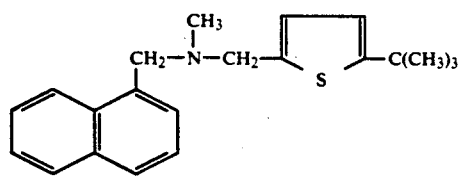

Compound 6 (Which is Included in the Compounds of the Formula IV)

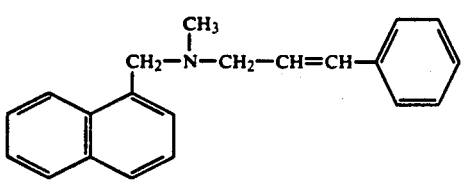

Compound 7 (Which is Included in the Compounds of the Formula V)

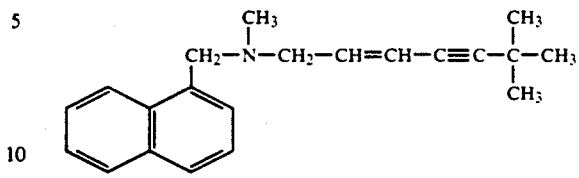

(1) In the same manner as in Example 1, the minimum inhibitory concentration (MIC, unit: μg/ml) of miconazole in combination with Compounds 2 to 7 at a concentration of 100 mg/ml, was examined.

The results are shown in Table 5. As is evident from Table 5, synergistic effects by the combined use were observed as in the case of Example 1.

TABLE 5

| | Minimum Inhibitory Concentration (MIC) μg/ml | |
|---|---|---|
| Aryl-methylamine antifungal agent | Nil | Imidazole antifungal agent (μg/ml) miconazole |
| Compound 2 | >100 | 3.13 |
| Compound 3 | >100 | 6.25 |
| Compound 4 | >100 | 1.56 |
| Compound 5 | >100 | 3.13 |
| Compound 6 | >100 | 1.56 |
| Compound 7 | >100 | 0.78 |
| Nil | | 25 |

(2) The effects of the combined use of Compound 6 or 7 with miconazole or ketoconazole were examined by the same disk method as in Example 1(3), whereby the same results as shown in FIGS. 2 and 3 were obtained, and thus remarkable synergistic effects of the combined use were observed.

EXAMPLE 3

To examine the acute toxicity of the arylmethylamine antifungal agents used in the composition of the present invention, Compounds 1 and 2 were selected, and they were, respectively, suspended in 0.5% methyl cellulose and orally administered to ICR male mice of 5 weeks old (body weight: 26-28 g) at a dose corresponding to the body weight.

Each compound was administered upto 5,000 mg/kg, whereby there was no instance of death, and no change in the general symptom after the administration was observed.

This indicates that the arylmethylamine antifungal agents have low toxicity. When they are combined with the azole antifungal agents, the content of the azole antifungal agents which have strong toxicity and unsuitable for administration in a large amount, can be substantially reduced by virtue of the synergistic effects of the combined use. This merit is significant.

As described in detail in the foregoing, the composition of the present invention using an azole antifungal agent and an arylmethylamine antifungal agent in combination, is an excellent antifungal agent which exhibits a remarkable synergistic effect by the combined use and which shows fungistatic and fungicidal effects at a low dose.

We claim:
1. An antifungal composition comprising:

synergistically effective amounts of the mixture of one member selected from the group consisting of miconazole, ketoconazole and fluconazole; and an arylmethylamine compound of the formula:
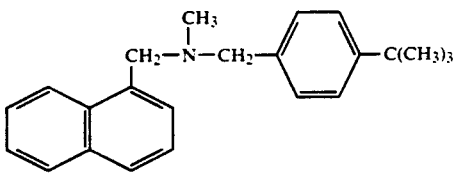
(N-4-tertbutylbenzyl-N-methyl-1-naphthalenemethylamine).
* * * * *